(12) United States Patent
Ramadoss et al.

(10) Patent No.: US 6,395,771 B1
(45) Date of Patent: May 28, 2002

(54) PACLITAXEL DERIVATIVES FOR THE TREATMENT OF CANCER

(75) Inventors: Sunder Ramadoss, New Delhi; Anand Vardhan, Ghaziabad; Manu Jaggi, Haryana; Arvind Kumar Sharma, Noida, all of (IN)

(73) Assignee: Dabur Research Foundation, Ghaziabad (IN)

( * ) Notice: Subject to any disclaimer, the term of this patent is extended or adjusted under 35 U.S.C. 154(b) by 0 days.

(21) Appl. No.: 09/584,113

(22) Filed: May 31, 2000

(51) Int. Cl.$^7$ .................. A61K 31/337; C07D 305/14
(52) U.S. Cl. .................. 514/449; 549/510; 549/511
(58) Field of Search .................. 514/449; 549/510, 549/511

(56) References Cited

U.S. PATENT DOCUMENTS 5,792,877 A * 8/1998 Murray et al. .............. 549/510

* cited by examiner

Primary Examiner—Ba K. Trinh
(74) Attorney, Agent, or Firm—Ladas & Parry

(57) ABSTRACT

The invention provides novel paclitaxel derivatives obtained by effecting modifications at $C_{2'}$, $C_{3'}$ and/or $C_7$ positions of paclitaxel, said derivatives being useful in inhibiting the growth of cancer of lung, breast, ovary, cervix or leukemia, and pharmaceutical compositions comprising such derivatives.

22 Claims, 3 Drawing Sheets

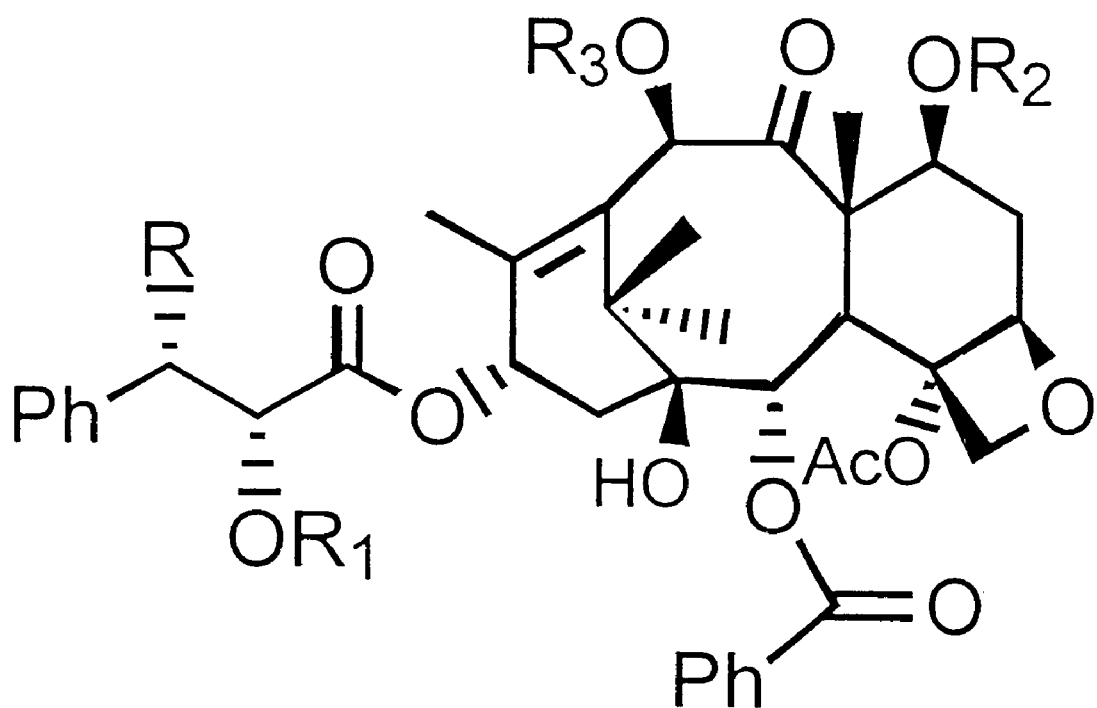
Fig : 2

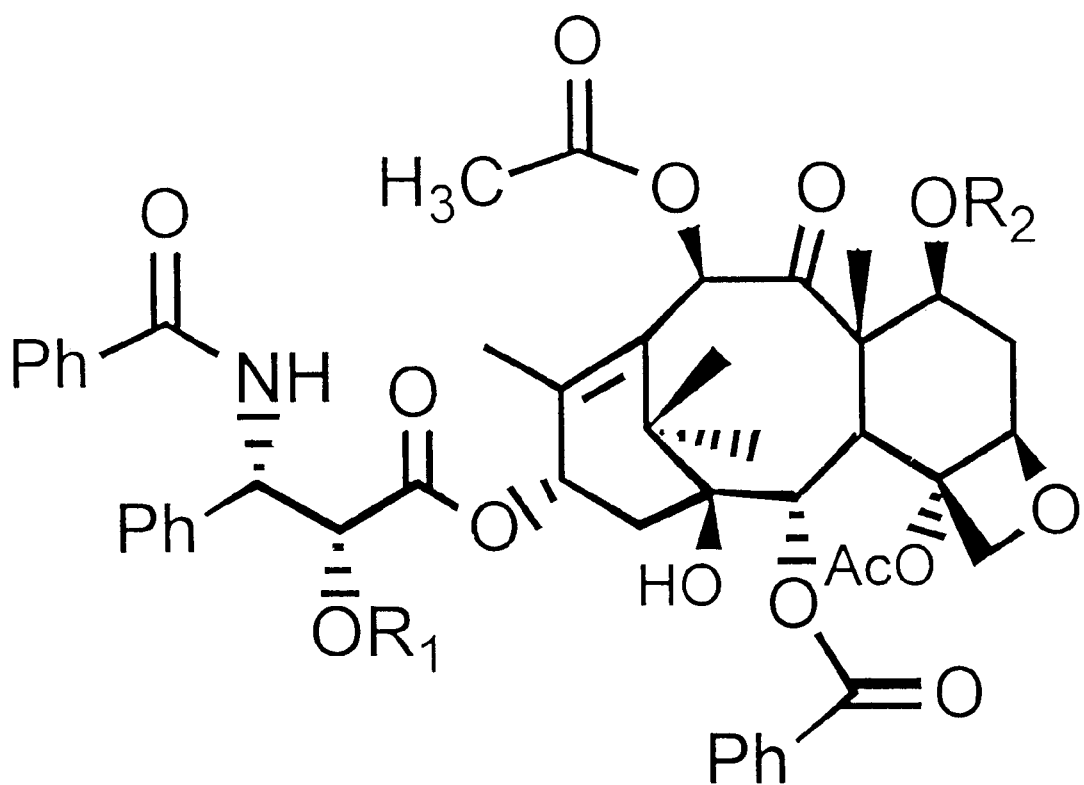
Fig : 3

PACLITAXEL DERIVATIVES FOR THE TREATMENT OF CANCER

FIELD OF INVENTION

The invention relates to novel paclitaxel derivatives useful in the treatment of cancer. More specifically, the invention relates to paclitaxel derivatives obtained by substitutions at the $C_2$, $C_3$, and/or $C_7$ positions. The invention also provides pharmaceutical compositions containing the said derivatives and useful in the treatment of cancer affecting the lung, breast, ovary, cervix, etc. Further, the invention provides methods for the preparation of such novel paclitaxel derivatives.

BACKGROUND OF THE INVENTION

Paclitaxel is a diterpenoid taxane derivative from the bark of Pacific yew, *Taxus brevifolia*. It was first discovered in 1971 following investigation of bark extracts from the European yew tree, *Taxus baccata*. Paclitaxel was randomly isolated and found to exhibit cytotoxic properties. The basic structure of paclitaxel is as depicted in FIG. 1. The central backbone unit of paclitaxel contains Baccatin III. Although Paclitaxel is structurally similar to vinca alkaloids, its mechanism of action is unique. It promotes the microtubule assembly by enhancing the action of tubulin dimers, stabilizing existing microtubules, and inhibiting their disassembly. Paclitaxel was originally approved for the treatment of refractory ovarian cancer and was subsequently approved for the use in breast carcinoma. It has also been used alone or as an adjunct therapy in other malignancies such as advanced head and neck cancer, metastatic breast cancer, non-small-cell lung cancer, acute leukemia, and melanoma.

Since paclitaxel shows great promise as a chemotherapeutic agent, several researchers have spent substantial time in developing potent derivatives of paclitaxel. Attachment of the C-13 side chain of paclitaxel to other naturally occurring taxanes and taxoids, modification of the diterpene moiety of paclitaxel at various centers such as 7-hydroxyl group, 10-hydroxyl group and modifications at C-2, 9, 19, 6 and 4 positions have been well documented. Other approaches have been modification at the C-13 side chain of paclitaxel, and in recent times, the development of water-soluble paclitaxel prodrugs.

Modifications at the diterpene moiety as well as the C-13 side chain of paclitaxel has resulted in several derivatives of paclitaxel which have shown varying cytotoxic activities on human tumor cell lines in in vitro assays. In the diterpene moiety of paclitaxel, the 4-acetyl group and the 2-benzoyloxy moiety of paclitaxel are essential structures for cytotoxicity. Modifications of the A-ring and B-ring did not affect microtubule binding in a significant way. The acetoxy group at C-10 can be deleted while esterification of the C-10 hydroxyl group with a variety of acids provided active compounds. Of all the modifications made on the diterpene portion of the molecule, most of the initial structural changes have involved the derivatisation of the 7-hydroxyl group. The 7-hydroxyl group can be modified or epimerized without significant loss of bioactivity. Examples include 7-acetyltaxol, 7-benzoyltaxol, 7-glutaryl derivatives, and C-7 amino acid esters. Modifications at C-19 may be tolerated without significant loss of bioactivity.

Most of the C-13 simplified paclitaxel derivatives and derivatives of different stereochemistry demonstrated reduced activity in comparison to paclitaxel. The 2'-hydroxyl and the 3'-benzamido group are not essential for bioactivity, but are important for strong microtubule binding and cytotoxicity. Formation of ethers at 2'-hydroxyl group, such as methyl ether and ter-butyldimethylsilyl ether, reduced cytotoxicity. Acetylation of the 2'-hydroxyl group (2'-acetyltaxol) also leads to loss of activity. Replacement of 2'-hydroxyl group by fluorine was also found to significantly reduce the cytotoxicity.

A problem associated with the systemic administration of Paclitaxel is its low solubility in most pharmaceutically acceptable solvents. Most formulations used clinically contain Cremophor EL (polyethoxylated castor oil) and ethanol as excipients, which may cause hypersensitivity reactions. This can be prevented by pre-medication with certain antihistaminic drugs. To eliminate this vehicle and possibly reduce the dose and hence toxicity of paclitaxel, several approaches of drug targeting are currently being worked upon. Much work is being done on formulation of paclitaxel in liposomes of various compositions. Paclitaxel-liposomes retain the growth-inhibitory activity of the free drug in vitro against a variety of tumor cell lines. In mice, paclitaxel-liposomes were well-tolerated when given in bolus doses (Sharma A., et al, Pharm Res: 11, 1994). The Maximum Tolerated Dose (MTD) was >200 mg/kg which exceeded that of free paclitaxel (MTD of 30 mg/kg by iv or 50 mg/kg by ip administration). Free paclitaxel administered in the Cremophor vehicle was toxic at doses >30 mg/kg, as was the equivalent volume of vehicle without drug. However, the low stability of these formulations is still an area of concern. Some of these formulations are physically and chemically stable for only 2 months at 4 degrees C., or for 1 month at 20 degrees C.

Yet another approach of tumor targeting is the administration of paclitaxel-loaded poly (lactic-co-glycolic acid) microspheres containing isopropyl myristate (Paclitaxel-IPM-PLGA-MS). After administration of the drug saline solution, paclitaxel disappears rapidly from plasma and distributes extensively in various tissues. The tissue levels of paclitaxel in the lung were found to be higher than those in plasma but relatively lower than those in kidneys, bile, and liver (Sato H. et al, Biol Pharm Bull: 19, 1996). The biodistribution of paclitaxel after administration of Paclitaxel-IPM-PLGA-MS (3 mg paclitaxel/kg), on the other hand, was altered significantly from the control (paclitaxel solution) group. Paclitaxel concentrations in the lung were increased significantly with the microsphere group. It was also noticed that the paclitaxel levels in the lung were maintained at relatively high levels. Thus, it may be possible to use Paclitaxel-IPM-PLGA-MS for targeted delivery of paclitaxel to the lung. It however remains to be seen if this strategy can be used for targeting paclitaxel to tumors other than lung.

Enzyme-activatable prodrugs in conjunction with antibody-enzyme fusion proteins offer an alternative to enhance the anti-tumor efficacy of antibodies and reduce the toxic side effects of conventional chemotherapeutics. Cephalosporins have proven to be highly versatile triggers for the enzymatic activation of such prodrugs. A cephem prodrug of paclitaxel (PROTAX) was synthesized by substituting the C-3' position of cephalothin with 2'-(gamma-aminobutyryl) paclitaxel (Rodrigues M. L., et al, Chem Biol: 2, 1995). Hydrolysis of PROTAX by beta-lactamase rapidly releases 2'-(gamma-aminobutyryl) which yields paclitaxel following intramolecular displacement. PROTAX is inactive in a microtubule assembly assay in vitro but has similar activity to paclitaxel following prolonged activation with beta-lactamase. PROTAX is approximately 10-fold less toxic than paclitaxel against SK-BR-3 breast tumor cells in vitro but has activity approaching that of paclitaxel following prolonged activation with a fusion protein comprising beta-lactamase fused to a tumor-targeting antibody fragment. Tubulin polymerization activity is abolished and cytotoxicity is reduced in the PROTAX prodrug compared to paclitaxel.

Li. C., et al have recently reported in Cancer Research, 1998, p.2404, that a water soluble poly (L-glutamic acid)-paclitaxel (PG-TXL) conjugate produces striking antitumor effects with diminished toxicity. A single intravenous injection of PG-TXL of 40 mg paclitaxel/kg resulted in the disappearance of an established implanted 13762F mammary adenocarcinoma. PG-TXL has a prolonged half-life in plasma and a greater uptake in tumor as compared with paclitaxel.

Abraham E. Mathew et. al, J.Med.Chem, p.145(1992) reports the synthesis and evaluation of water soluble 2' and 7-amino acid derivatives of paclitaxel with antitumor activity.

Renee Paradis and Michel Page, Anticancer Research, 1998 p.2711 reports new active paclitaxel amino acid derivatives with improved water solubility.

JP 09235225 discloses the C2'-(un)protected amino acid residue and peptide residue conjugates of paclitaxel which have shown in vivo efficacy in guinea pigs implanted with melanoma cells.

U.S. Pat. No. 5,719,265 deals with the synthesis of N-protected amino acid derivatives at 2'7-position, 2'-position amino acid is cleaved and then the 7-position amino acid is deprotected which improves the solubility and their use as anti tumor agent. EP 0747385A1 discloses the synthesis of paclitaxel analogues modification at 2'-position and 3'-amino position as different benzoyl derivatives and their use as antitumor agents.

Indian Journal of Chemistry, Vol.38B, p.1194 (1999) deals with the anticancer activities of $C_2$ modified paclitaxel analogues.

U.S. Pat. No. 5,917,062 teaches the utilization of new $C_7$ alkyl carbonate or alkyl carbonyl derivative of 10-Deacetyl Baccatin III for preparation of semisynthetic paclitaxel and its analogues.

U.S. Pat. No. 6,017,935 provides $C_7$-substituted sulphur analogues of paclitaxel having anti-tumor activity, pharmaceutical formulations and methods for the preparation thereof.

Thus, several workers have developed different analogues of paclitaxel. Still, there is a need for analogues that alleviate toxic side effects and provide improved dose therapy. It is towards this goal that the applicants have worked and developed novel paclitaxel analogues.

OBJECTS OF THE INVENTION

The main object of the invention is to provide novel paclitaxel derivatives obtained by modifying effecting modifications $C_{2'}$, $C_{3'}$ and/or $C_7$ positions of paclitaxel, said derivatives being useful in the treatment of cancer.

Another object is to provide pharmaceutical compositions containing the said novel paclitaxel analogues, useful in inhibiting tumor growth and, particularly, for inhibiting the growth of cancer of lung, breast, ovary, cervix or leukemia.

It is also an object of the invention to provide pharmaceutical compositions in improved dosage so that the toxic and adverse reactions associated with paclitaxel derivatives are reduced.

Yet another object of the invention is to reduce/or eliminate the hypersensitivity reactions caused by Cremophor EL.

Still another object is to provide a methods for the preparation of novel paclitaxel derivatives modified at $C_{2'}$, $C_{3'}$ and/or $C_7$ positions.

SUMMARY OF THE INVENTION

The invention provides novel paclitaxel derivatives obtained by effecting modifications at $C_{2'}$, $C_{3'}$ and/or $C_7$ positions of paclitaxel, said derivatives being useful in inhibiting the growth of cancer of lung, breast, ovary, cervix or leukemia. Further, the invention provides pharmaceutical compositions employing the novel paclitaxel derivatives of the invention. In addition, the invention prescribes so that, the toxic and adverse reactions commonly observed with paclitaxel are reduced. Further, the invention provides pharmaceutical compositions employing excipients, which reduce or eliminate the hypersensitivity reactions generally observed by the use of Cremophor EL. The invention also teaches methods for the synthesis of the paclitaxel analogues of the invention are obtained primarily by sulphonation, acylation, benzoylation and/or condensation reactions.

BRIEF DESCRIPTION OF THE ACCOMPANYING DRAWINGS

In the drawings that accompany

FIG. 2 represents the structural formula of paclitaxel analogues of the invention.

FIG. 3 represents the structural formula of preferred paclitaxel analogues of the invention.

DETAILED DESCRIPTION OF THE INVENTION

Figure 1:
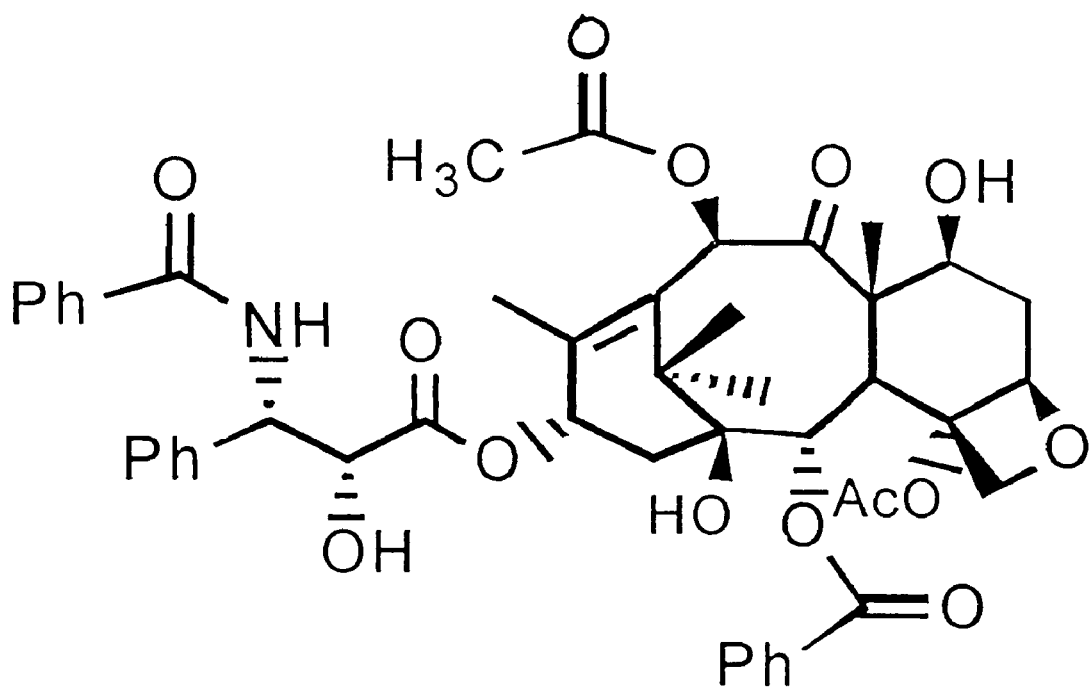
FIG. 1 represents the structural formula of Paclitaxel.

As mentioned in the foregoing sections, Baccatin III forms the basic structural unit of paclitaxel. Typically, novel analogues are developed without disturbing the basic structure of paclitaxel so that the most potent and effective cytotoxic compounds are obtained.

The applicants have found that substitutions at $C_{2'}$, $C_{3'}$ and $C_7$ positions of paclitaxel yield acyl, benzoyl, amino acid and peptide analogues which exhibit greater cytotoxicity than paclitaxel. According to the invention, the paclitaxel analogues thus obtained are represented by the general formula as shown in FIG. 2 of the accompanying drawings. The analogues thus formed are useful in the treatment of leukemia, ovary, breast, lung and cervical cancer.

In particular, the applicants have observed that the $C_{2'}$, position of paclitaxel are quite reactive and the site can be utilized to develop useful and potent paclitaxel analogues. Condensation and other reactions at this site have produced several amino acid, benzoyl, acyl, thioaryl, protected and unprotected amino acid and peptide analogues and their salts. Some examples of such analogues are represented in the description of FIG. 2 that follows.

In addition, the applicants observed that the $C_{3'}$ amino function is also very reactive and acylation benzoylation or sulphonation at this site results in novel amide or sulphonamide derivatives respectively as represented in FIG. 2.

Wherein R, $R_1$, $R_2$, & $R_3$ either separately or in combination represent

R=—NHCOC$_6$H$_n$X [(n=0 to 5) [X=H, OH, Cl, Br, I, F, CN, NO$_2$, NH$_2$, CF$_3$, —OC$_n$H$_{2n+1}$, (n=1 to 4), C$_n$H$_{2n+1}$ (n=1 to 8)], —NHSO$_2$C$_6$F$_5$, —NHSO$_2$C$_6$H$_4$X (X=H, OH, OCH$_3$, NO$_2$, NH$_2$, OC$_2$H$_5$, Br, Cl, I, F, CH$_3$, C$_2$H$_5$) and/or NHSO$_2$C$_n$H$_{2n+1}$ (n=1 to 7)

$R_1$=—COCH$_2$NHCOCH$_2$NHBOC(t), —COCH$_2$NHCOCH$_2$NH$_2$, COCH$_2$NHCOCH$_2$NH$_2$.

$CH_3SO_3H$, $-COCH_2NHCOCH_2NH_2$, HCl, $-COCH_2NHCOCH_2NHCOC_6H_5$, $-COCH(OCOCH_3)CH_3$, $-COOCH_2CCl_3$, $-COCH(NHBOC-t)CH(CH_3)_2$, $-COCH(NH_2.CH_3SO_3H)CH(CH_3)_2$, $-COCH(NH_2.HCl)CH(CH_3)_2$, $-COCH(NHBOC-t)CH_2CH(CH_3)_2$, $-COCH(NH_2.CH_3SO_3H)CH_2CH(CH_3)_2$, $-COCH(NH_2.HCl)CH_2CH(CH_3)_2$, $-COCH_2NHBOC(t)-COCH_2NH_2$. $CH_3SO_3H$, $-COCH_2NH_2.HCl$, $-COCH_2C(CH_3)_2COOH$, $-COC(CH_3)_2CH_2COOH$ $-COCH(OH)CH(Ph)NH_2$, $-COCH_2NHCOCH_2NHCOC_6H_nX$ $COCH(OH)CH(Ph)NHCOC_6H_nX$, $COC_6H_nX$, [(n=0 to 5) X=H, OH, Cl, Br, I, F, CN, $NO_2$, $NH_2$, $CF_3$, $OC_nH_{2n+1}$, (n=1 to 4), $C_nH_{2n+1}$ (n=1 to 8), $-SO_2C_6F_5$,], $-SO_2C_6H_4X$ (X=H, OH, $OCH_3$, $OC_2H_5$, $NO_2$, $NH_2$, Br, Cl, I, F, $CH_3$, $C_2H_5$), $-SO_2C_nH_{2n+1}$ (n=1 to 7), $-COCH=C(CH_3)_2$, $-COC(CH_2Cl)(CH_3)_2$, $-COC(CH_3)_3$, $-COCH(OCOCH_3)C_6H_5$, $-COCH_2SC_6H_5$, $COOCH_2CCl_3$ and/or $COCH_2OCOCH_3$ $R_2=H$, $-COCH_3$, $-COOCH_2CCl_3$, $-COCH(OCOCH_3)CH_3$, $-COCH_2NHCOCH_2NHBOC(t)$, $-COCH_2NHCOCH_2NH_2$. $CH_3SO_3H$, $-COCH_2NHCOCH_2NH_2.HCl$, $-COCH(OH)CH(Ph)NH_2$, $-COCH(OH)CH(Ph)NH_2.HCl$, $-COCH(OH)(HCPh)NH_2.CH_3SO_3H$, $-COCH(OH)CH(Ph)NHCOOC(CH_3)_3$ $-COCH_2C(CH_3)_2COOH$ $COCH(OH)CH(Ph)NHCOC_6H_nX$ $-COCH_2NHCOCH_2NHCOC_6H_nX$, and/or $COC_6H_nX$ [(n=0 to 5) [X=H, OH, Cl, Br, I, F, CN, $NO_2$, $NH_2$, $CF_3$, $OC_nH_{2n+1}$, (n=1 to 4), $C_nH_{2n+1}$ (n=1 to 8)], $R_3=H$ or $-COCH_3$ The preferred paclitaxel analogues obtained by effecting modifications at $C_{2'}$, $C_{3'}$ and $C_7$ positions of paclitaxel are represented by the structural formula shown in FIG. 3.
Wherein $R_1=-COCH_2C(CH_3)_2COOH$, $-COC(CH_3)_2CH_2COOH$, $-COC_6H_3F_2(2,4)$, $-COC_6H_3F_2(2,3)$,
$-COC_6H_2F_3(2,3,4)$-$COC_6H_4CF_3(3)$
$-COCH_2NHCOCH_2NHCOOC(CH_3)_3$,
$-COCH_2NHCOCH_2NH_2.CH_3SO_3H$
$-COCH_2NHCOCH_2NH_2.HCl$,
$-COCH_2NHCOCH_2NHCOC_6H_5$,
$COCH_2NHCOCH_2NHCOC_6H_3F_2(2,3)$,
$-COCH_2NHCOCH_2NHCOC_6H_3F_2(2,4)$,
$COCH_2NHCOCH_2NHCOCH_6H_2F_3(2,3,4)$,
$-COCH_2SC_6H_5$, $-COCH_2COCH_3$,
$-COOCH_2CCl_3$, $-COCH(OCOCH_3)C_6H_5$.

$R_2=H$, $-COCH(OH)CH(Ph)NH_2$, $-COCH(OH)CH(Ph)NH_2.HCl$, $COCH(OH)CH(Ph)NH_2.CH_3SO_3H$, $-COCH(OH)CH(Ph)NHCOC_6H_5$, $-COCH(OH)CH(Ph)NHCOC_6H_3F_2(2,3)$, $-COCH(OH)CH(C_6H_5)NHCOC_6H_3F_2(2,4)$, $-COCH(OH)CH(C_6H_5)NHCOC_6H_2F_3(2,3,4)$, $-COCH(OH)CH(C_6H_5)NHCOOC(CH_3)_3$, $-COCH_2C(CH_3)_2COOH$, and/or $-COCH(OCOCH_3)CH_3$ The said preferred analogues of paclitaxel comprise acyl, benzoyl, amino acid and peptide analogues, which are also represented in Table I for easy reference.

TABLE I

Preferred acyl analogues are:- AV-82B, AV-82C, AV-125S, AV-126S, AV-147A & AV-15OS.

| Derivative | $R_1$ | $R_2$ |
|---|---|---|
| AV-82B | $-COCH_2C(CH_3)_2COOH$ | H |
| AV-82C | $-COC(CH_3)_2CH_2COOH$ | H |

TABLE I-continued

| | | |
|---|---|---|
| AV-125S | $-COCH(OCOCH_3)C_6H_5$ | H |
| AV-126S | $-COOCH_2CCl_3$ | $-COCH(OCOCH_3)CH_3$ |
| AV-147A | $-COCH_2COCH_3$ | H |
| AV-150S | $-COCH_2 SC_6H_5$ | H |

Preferred benzoyl analogues are:- AV-86B, AV-103S, AV-105S & AV-209S.

| Derivative | $R_1$ | $R_2$ |
|---|---|---|
| AV-86B | $-COC_6H_4CF_3(3)$ | H |
| AV-103S | $-COC_6H_3F_2(2,4)$ | H |
| AV-105S | $-COC_6H_3F_2(2,3)$ | H |
| AV-209S | $-COC_6H_3F_2(2,3,4)$ | H |

Preferred amino acid analogues are:-
AV-76B, AV-249S, AV-251S, AV-254S, AV-256S, AV-257B, AV-258S, AV-265S and AV-272S.

| Derivative | $R_1$ | $R_2$ |
|---|---|---|
| AV-76B | H | $-COCH(OH)CH(C_6H_5)NH_2$ |
| AV-249S | H | $-COCH(OH)CH(C_6H_5)NH\ COC_6H_3F_2(2,3,4)$ |
| AV-251S | H | $-COCH(OH)CH(C_6H_5)NHCOC_6H_5$ |
| AV-254S | H | $-COCH(OH)CH(C_6H_5)NH\ COC_6H_3F_2(2,4)$ |
| AV-256S | H | $-COCH(OH)CH(C_6H_5)NH_2.HCl$ |
| AV-257B | H | $-COCH_2C(CH_3)_2COOH$ |
| AV-258S | H | $-COCH(OH)CH(C_6H_5)NH_2.CH_3SO_3H$ |
| AV-265S | H | $-COCH(OH)CH(C_6H_5)NHCOC_6H_3F_2(2,3)$ |
| AV-272S | H | $-COCH(OH)CH(C_6H_5)NHCOOC(CH_3)_3$ |

Preferred peptides analogues are:- AV-4S, AV-259S, AV-260S, AV-261S, AV-262S, AV263S & AV-264S.

| Derivative | $R_1$ | $R_2$ |
|---|---|---|
| AV-4S | $-COCH_2NHCOCH_2NHBOC(t)$ | H |
| AV-259S | $-COCH_2NHCOCH_2NH_2.HCl$ | H |
| AV-260S | $-COCH_2NHCOCH_2NH_2CH_3SO_3H$ | H |
| AV-261S | $-COCH_2NHCOCH_2NHCOC_6H_5$ | H |
| AV-262S | $-COCH_2NHCOCH_2NHCOC_6H_3F_2(2,3)$ | H |
| AV-263S | $-COCH_2NHCOCH_2NHCOC_6H_3F_2(2,4)$ | H |
| AV-264S | $-COCH_2NHCOCH_2NHCOC_6H_2F_3(2,3,4)$ | H |

Pharmacuetical Compositions Containing Novel Derivatives of Paclitaxel

The present invention also provides various pharmaceutical compositions containing the novel derivatives of paclitaxel that are useful in the treatment of acute leukemia and cancer affecting the ovary, breast, lung, and cervix. These pharmaceutical compositions may be in various physical forms such as injections, syrups, tablets, lozenges, powders, aqueous or oily suspensions, syrups, elixirs, implants etc. Pharmaceutical compositions using novel paclitaxel analogues may be formed in conjunction with appropriate carriers and additives. The amount of the paclitaxel analogues in these compositions will vary depending on the physical form and mode of administration thereof. The ratio of the analogues to the carriers can be easily and readily determined by one skilled in the art at the time of administration of the composition. In any case, it is recommended that an amount of about 15 to 1500 mg of the novel paclitaxel analogues and preferably 75 to 750 mg of these analogues may be used in the composition.

The said compositions may be made in various physical forms and may contain physiologically acceptable diluents, fillers, lubricants, excipients, solvents, binders, stabilizers, and the like. Diluents that may be used in the compositions include but are not limited to dicalcium phosphate, calcium sulphate, lactose, cellulose, kaolin, mannitol, sodium chloride, dry starch, powdered sugar and for prolonged release tablet-hydroxypropyl methyl cellulose (HPMC). The binders that may be used in the compositions include but are not limited to starch, gelatin and fillers such as sucrose, glucose, dextrose and lactose.

Natural and synthetic gums that may be used in the compositions include but are not limited to sodium alginate, ghatti gum, carboxymethyl cellulose, methyl cellulose, polyvinyl pyrrolidone and veegum. Excipients that may be used in the compositions include but are not limited to microcrystalline cellulose, calcium sulfate, dicalcium phosphate, starch, magnesium stearate, lactose, and sucrose. Stabilizers that may be used include but are not limited to polysaccharides such as gelatin and synthetic and semi-synthetic polymers such as carbomer resins, cellulose ethers and carboxymethyl chitin.

Solvents used include but are not limited to Ringer's solution, water, distilled water, dimethyl sulfoxide to 50% in water, propylene glycol (neat or in water), phosphate buffered saline, balanced salt solution, glycol and other conventional fluids.

The nature of pharmaceutical composition employed will, of course, depend on the desired route of administration. The dosage of the composition for human is in the range of about 10 to 1000 mg/m$^2$/day and the preferred range is about 50 to 500 mg/m$^2$/day.

Compositions which provide from about 1 mg to 1000 mg of the composition per unit dose are preferred.

According to the invention, methods of treatment of humans comprise the steps of administration of a therapeutically effective amount of the paclitaxel analogues of the invention to the subject in need thereof. Administration of the pharmaceutical composition of the invention will depend upon the physical form of the composition. Injections may be administered systemically, or may be transdermal and parentral (i.e., intramuscular, intraperitoneal, subcutaneous or intravenous). Tablets are administered orally. In accordance with good clinical practice, it is preferred to administer the composition at a dose that will produce anticancer effects without causing undue harmful side effects. The composition may be administered either alone or in combination with other anticancer agents.

Methods of Preparation of Paclitaxel Derivatives

The paclitaxel analogues of the invention are prepared employing methods selected from esterification or condensation, acylation, sulphonation and the like. Representative examples of such methods are described and set out hereinbelow.

The general method of production of the paclitaxel analogues of the invention comprises the steps of:
 (i) dissolving paclitaxel in an organic solvent and treating it with a suitable reagent,
 (ii) quenching the reaction by adding chilled water followed by extraction with an organic solvent;
 (iii) separating the organic layer by conventional methods and washing the same with very dilute acid and water; and
 (iv) drying the residue over anhydrous sodium sulphate, filtering and evaporating the solvent to dryness to yield crude paclitaxel derivative which is crystallized using organic solvent to yield pure analogues.

Conventional procedures known to those skilled in the art can be used in the preparation of the various paclitaxel derivatives wherein the starting material is paclitaxel or a derivative thereof unless otherwise specifically mentioned. The procedures mentioned below are either used alone or in combination to produce the novel derivatives. In examples below the term "substrate" refers to paclitaxel or its derivatives as starting material unless otherwise indicated.

The specific examples that follow illustrate the synthesis of some of the representative compounds of the invention and are not to be construed as limiting the invention in sphere or scope. Further, modifications or departures in the structure, the pharmaceutical compositions or the methods of preparation thereof that may be apparent to those in the art are deemed to fall within the scope of the invention.

Preparation of Paclitaxel Derivatives

Preparation of 2'-O-benzoyl and 2',7-di-O-benzoyl Derivative Method-I
 i) treating paclitaxel or its derivative (having C-2' or C-7-hydroxy groups) in methylene chloride and pyridine with suitable benzoyl chloride derivative for approximately 6 to 16 hrs at ambient temperature.
 ii) adding water to work up the reaction mixture of step (1), extracting with organic solvent to obtain organic layer.
 iii) drying the organic layer over anhydrous sodium sulphate and evaporating the solvent,
 iv) purifying the residue by column chromatography to yield pure benzoyl derivative.

In one embodiment the benzoyl chloride derivatives used in step (1) are represented by general formula $C_6H_nXCOCl$ wherein (n=2 to 4), $C_{10}H_nXCOCl$ (n=2 to 6) [(X=Cl, Br, I, F, $CF_3$, $CH_2Cl_2$, $NO_2$, OH, $OCH_3$, $OC_2H_5$, $C_nH_{2n+1}$, (n=1 to 7)].

In another embodiment, the organic bases are selected from pyridine, piperidine and 4-dimethylamino pyridine.

Method-II
 i) treating paclitaxel or its derivative (having C-2' or C-7-hydroxy groups) in methylene chloride in presence of DCC (Dicyclohexylcarbodiimide) and catalytic amount of DMAP (4-dimethylamino pyridine) with suitable benzoic acid derivative represented by general formula $C_6H_nXCOOH$ (n=2 to 4) [X=Cl, Br, I, F, $CF_3$, $CH_2Cl_2$, $NO_2$, $NH_2$, OH, $OCH_3$, $OC_2H_5$, $C_nH_{2n+1}$, (n=1 to 7)] at ambient temperature for approximately 4 to 16 hrs.
 ii) filtering the insoluble residue of the reaction mixture and washing the filtrate with water,
 iii) drying the organic layer over anhydrous sodium sulphate and evaporating the organic solvent to obtain residue which is purified by column chromatography to yield pure benzoyl derivative.

Preparation of 2' and 2',7-di-O-(N-protected Amino Acid)
 i) A solution of paclitaxel in methylene chloride is allowed to react at ambient temperature with N-protected amino acid in presence of DCC and a catalytic amount of 4-dimehtylaminopyridine approximately for 16 to 24 hrs at ambient temperature.
 ii) Filtering the insoluble of the reaction mixture and then washing the filtrate with water.
 iii) drying the organic layer over anhydrous sodium sulphate and evaporating the organic solvent to obtain a residue which is purified by column chromatography to yield pure.

Preparation of 2'-O-acyl Derivatives of Paclitaxel
 i) treating the paclitaxel or its derivative (having C-2' and/or C-7-hydroxy groups) in methylene chloride and pyridine or in pyridine with suitable anhydride (saturated or unsaturated) for approximately 18 to 24 hrs at ambient temperature.
 (ii) evaporating the reaction mixture by adding water and extracting with organic solvent.
 (iii) drying the organic layer over anhydrous sodium sulphate and evaporating the solvent,
 iv) purification of the residue obtained by column chromatography to yield pure $C_2$-O-acyl derivative of paclitaxel The organic bases used are TEA, Pyridine and 2-dimethylaminopyridine (DMAP).

Examples of anhydride that can be used in this process are represented by the general formula $(RCH_2CO)_2O$ wherein $R=H$, $CH_3$, $C_2H_5$ or acyl chloride.

Preparation of 3'-N-Benzoyl Derivatives
  i) treating 3' amino compound of paclitaxel in ethylacetate with suitable benzoyl chloride in presence of aqueous solution of sodiumbicarbonate solution for approximately 2 to 6 hrs. at ambient temperature,
  ii) separating the organic layer of step(I) and washing with water,
  iii) drying the organic layer over anhydrous sodium sulphate and evaporating the solvent, purifying the residue obtained by column chromatography to yield 3'-N-benzoyl derivative of paclitaxel.

Preparation of 3'-sulphonamide Derivatives
  i) treating the substrate (having $C_{3'}$ amino group) in ethylacetate and saturated aqueous solution of sodium bicarbonate with suitable sulphonyl chloride for 6 hr–24 hr at ambient temperature.
  ii) separating the organic layers and washing the organic layer with water.
  iii) drying the organic layer over sodium sulphate and evaporating the solvent purifying the residue obtained by column chromatography to yield pure $C_{3'}$-sulphonamide derivative.

In vitro cytotoxicity assay

In vitro cytotoxic activity of novel paclitaxel derivatives was determined by performing the MTT cytotoxicity assay (Mosmann T., J Immunological Methods, 65:55; 1983). Briefly, the cultured tumor cells were separately seeded in a 96-well culture plate and co-incubated with paclitaxel or its derivatives dissolved in methanol, dimethyl formamide, dimethyl sulfoxide or isopropyl alcohol with relevant controls at 37° C. in a $CO_2$ incubator. After 24 to 96 hours, the assay was terminated and percent cyotoxicities calculated. Table II shows anticancer potency of paclitaxel derivatives over paclitaxel in leukemia cells (MOLT-4), ovarian cancer cells (PA-1), breast cancer cells (HBL100), lung cancer cells (L132) and cervical cancer cells (SiHa).

TABLE II

POTENCY OF NOVEL PACLITAXEL DERIVATIVES WITH RESPECT TO PACLITAXEL ON VARIOUS CANCER CELL LINES

| Code No | Potency | | | | |
|---|---|---|---|---|---|
| | MOLT-4 | SiHa | PA-1 | HBL100 | L132 |
| AV-4S | 13.2 | — | 9.5 | 3.3 | 56.3 |
| AV-76B | — | — | 90 | 5.0 | — |
| AV-82B | — | >25.0 | — | >170 | — |
| AV-86B | — | 2.5 | — | <PT | ND |
| AV-103S | — | 1.4 | — | ND | — |
| AV-105S | — | 1.4 | — | 3.8 | — |
| AV-125S | — | — | =PT | — | — |
| AV-126S | — | — | =PT | — | — |
| AV-135S | — | — | ND | — | — |
| AV-147A | — | — | =PT | — | — |
| AV-150S | — | — | =PT | — | — |

—: Not active
ND: Not Done
=PT: Activity equivalent to Paclitaxel
<PT: Activity less than Paclitaxel

We claim:
1. A derivative of paclitaxel of the formula

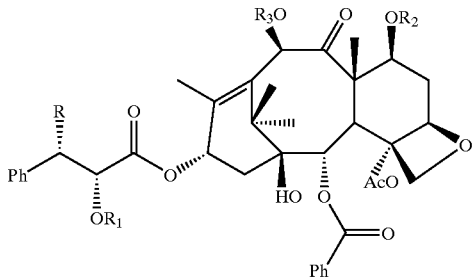

wherein R is $—NHCOC_6H_aX$ (a is 0 to 4) (X is H, OH, Cl, Br, I, F, CN, $NO_2$, $NH_2$, $CF_3$, $—OC_bH_{2b+1}$, (b is 1 to 4), $C_cH_{2c+1}$ (c is 1 to 8)), $—NHSO_2C_6F_5$, $—NHSO_2C_6H_4Y$ (Y is H, OH, $OCH_3$, $NO_2$, $NH_2$, $OC_2H_5$, Br, Cl, I, F, $CH_3$, or $C_2H_5$) or $NHSO_2C_dH_{2d+1}$ (d is 1 to 7);

$R_1$ is $—COCH_2NHCOCH_2NHBOC(t)$, $—COCH_2NHCOCH_2NH_2$, $COCH_2NHCOCH_2NH_2CH_3SO_3H$, $—COCH_2NHCOCH_2NH_2HCl$, $—COCH_2NHCOCH_2NHCOC_6H_5$, $—COCH(OCOCH_3)CH_3$, $—COOCH_2CCl_3$, $—COCH(NHBOC-t)CH(CH_3)_2$, $—COCH(NH_2CH_3SO_3H)CH(CH_3)_2$, $—COCH(NH_2.HCl)CH(CH_3)_2$, $—COCH(NHBOC-t)CH_2CH(CH_3)_2$, $—COCH(NH_2.CH_3SO_3H)CH_2CH(CH_3)_2$, $—COCH(NH_2.HCl)CH_2CH(CH_3)_2$, $—COCH_2NHBOC(t)$, $—COCH_2NH_2CH_3SO_3H$, $—COCH_2NH_2.HCl$, $COCH_2C(CH_3)_2COOH$, $—COC(CH_3)_2CH_2COOH$, $—COCH(OH)CH(Ph)NH_2$, $—COCH_2NHCOCH_2NHCOC_6H_aZ$, $COCH(OH)CH(Ph)NHCOC_6H_aZ$, $COC_6H_aZ$ (a is 0 to 4) (Z is H, OH, Cl, Br, I, F, CN, $NO_2$, $NH_2$, $CF_3$, $OC_bH_{2b+1}$, (b is 1 to 4), $C_cH_{2c+1}$ (c is 1 to 8), or $—SO_2C_6F_5$), $—SO_2C_6H_4A$ (A is H, OH, $OCH_3$, $OC_2H_5$, $NO_2$, $NH_2$, Br, Cl, I, F, $CH_3$, or $C_2H_5$), $—SO_2C_dH_{2d+1}$ (d is 1 to 7), $—COCH=C(CH_3)_2$, $—COC(CH_2Cl)(CH_3)_2$, $—COC(CH_3)_3$, $—COCH(OCOCH_3)C_6H_5$, $—COCH_2SC_6H_5$, $COOCH_2CCl_3$ or $COCH_2OCOCH_3$;

$R_2$ is H, $—COCH_3$, $—COOCH_2CCl_3$, $—COCH(OCOCH_3)CH_3$, $—COCH_2NHCOCH_2NHBOC(t)$, $—COCH_2NHCOCH_2NH_2.CH_3SO_3H$, $—COCH_2NHCOCH_2NH_2.HCl$, $—COCH(OH)CH(Ph)NH_2$, $—COCH(OH)CH(Ph)NH_2HCl$, $—COCH(OH)(CHPh)NH_2CH_3SO_3H$, $—COCH(OH)CH(Ph)NHCOOC(CH_3)_3$, $—COCH_2C(CH_3)_2COOH$, $COCH(OH)CH(Ph)NHCOC_6H_aX$, $—COCH_2NHCOCH_2NHCOC_6H_aX$, or $COC_6H_aX$ (a is 0 to 4) (X is H, OH, Cl, Br, I, F, CN, $NO_2$, $NH_2$, $CF_3$, $OC_bH_{2b+1}$ (b is 1 to 4), or $C_cH_{2c+1}$ (c is 1 to 8)); and $R_3$ is H or $—COCH_3$.

2. A paclitaxel derivative as claimed in claim 1 of the formula

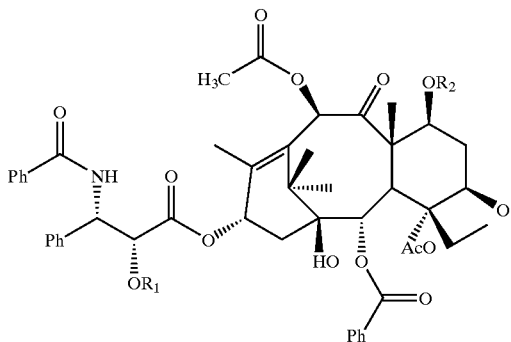

wherein

R$_1$ is —COCH$_2$C(CH$_3$)$_2$COOH, —COC(CH$_3$)$_2$CH$_2$COOH, —COC$_6$H$_3$F$_2$(2,4), —COC$_6$H$_3$F$_2$(2,3), —COC$_6$H$_2$F$_3$(2,3,4), —COC$_6$H$_4$CF$_3$(3), —COCH$_2$NHCOCH$_2$NHCOOC(CH$_3$)$_3$, —COCH$_2$NHCOCH$_2$NH$_2$·CH$_3$SO$_3$H, —COCH$_2$NHCOCH$_2$NH$_2$·HCl, —COCH$_2$NHCOCH$_2$NHCOC$_6$H$_5$, —COCH$_2$NHCOCH$_2$NHCOC$_6$H$_3$F$_2$(2,3), —COCH$_2$NHCOCH$_2$NHCOC$_6$H$_3$F$_2$(2,4), —COCH$_2$NHCOCH$_2$NHCOC$_6$H$_2$F$_3$(2,3,4), —COCH$_2$SC$_6$H$_5$, —COCH$_2$COCH$_3$, —COOCH$_2$CCl$_3$, —COCH(OCOCH$_3$)C$_6$H$_5$; and R$_2$ is H, —COCH(OH)CH(Ph)NH$_2$, —COCH(OH)CH(Ph)NH$_2$·HCl, —COCH(OH)CH(Ph)NH$_2$·CH$_3$SO$_3$H, —COCH(OH)CH(Ph)NHCOC$_6$H$_5$, —COCH(OH)CH(Ph)NHCOC$_6$H$_3$F$_2$(2,3), —COCH(OH)CH(C$_6$H$_5$)NHCOC$_6$H$_3$F$_2$(2,4), —COCH(OH)CH(C$_6$H$_5$)NHCOC$_6$H$_2$F$_3$(2,3,4), —COCH(OH)CH(C$_6$H$_5$)NHCOOC(CH$_3$)$_3$, —COCH$_2$C(CH$_3$)$_2$COOH, or —COCH(OCOCH$_3$)CH$_3$.

3. The method for treating cancer, said method comprising the step of administering a therapeutically effective amount of a paclitaxel derivative as claimed in claim 1 or a combination thereof to a patient in need of said treatment.

4. The method as claimed in claim 3, wherein the cancer afflicts the lung, breast, ovary, cervix or is leukemia.

5. The method as claimed in claim 3, wherein said patient is a human, mammal or other animal.

6. The method as claimed in claim 3, wherein the dosage for humans is in the range of 15 to 1500 mg/m$^2$/day.

7. The method as claimed in claim 3, wherein the dosage for humans is 10 to 1000 mg per unit dose of paclitaxel derivative.

8. The method as claimed in claim 3, wherein the paclitaxel derivative is administered with a pharmaceutically acceptable additive, carrier, diluent, solvent, filler, lubricant, excipient, binder or stabilizer.

9. The method as claimed in claim 3, wherein the paclitaxel derivative is administered in the form of a tablet, lozenge, capsule, powder, aqueous or oily suspension, syrup, elixir, implant or aqueous solution.

10. The method as claimed in claim 3, wherein the paclitaxel derivative is administered to a patient systemically or orally.

11. A method for treating cancer, said method comprising the step of administering a therapeutically effective amount of a paclitaxel derivative as claimed in claim 2 or a combination thereof to a patient in need of said treatment.

12. The method as claimed in claim 11, wherein the cancer afflicts the lung, breast, ovary, cervix or is leukemia.

13. The method as claimed in claim 11, wherein said patient is a human, mammal or other animal.

14. The method as claimed in claim 11, wherein the dosage for humans is in the range of 15 to 1500 mg/m$^2$/day.

15. The method as claimed in claim 11, wherein the dosage for humans is 10 to 1000 mg per unit dose of paclitaxel derivative.

16. The method as claimed in claim 11, wherein the paclitaxel derivative is administered with a pharmaceutically acceptable additive, carrier, diluent, solvent, filler, lubricant, excipient, binder or stabilizer.

17. The method as claimed in claim 11, wherein the paclitaxel derivative is administered in the form of a tablet, lozenge, capsule, powder, aqueous or oily suspension, syrup, elixir, implant or aqueous solution.

18. The method as claimed in claim 11, wherein the paclitaxel derivative is administered to a patient systemically or orally.

19. A composition comprising a paclitaxel derivative as claimed in claim 1 and a pharmaceutically acceptable additive, diluent, solvent filler, lubricant, excipient, binder or stablizer.

20. The composition according to claim 11, further comprising an anticancer drug.

21. A composition comprising a paclitaxel derivative as claimed in claim 2 and a pharmaceutically acceptable additive, diluent, solvent filler, lubricant, excipient, binder or stabilizer.

22. The composition according to claim 21, further comprising an anticancer drug.

* * * * *